United States Patent [19]
Henwood

[11] Patent Number: 5,813,992
[45] Date of Patent: Sep. 29, 1998

[54] SINGLE USE INDICATOR FOR STETHOSCOPES

[76] Inventor: Peter S. W. Henwood, 72 New Bond Street, London, England, W1Y 9DD

[21] Appl. No.: 859,653

[22] Filed: May 20, 1997

[51] Int. Cl.⁶ ........................................... A61B 00/00
[52] U.S. Cl. ................................................. 600/528
[58] Field of Search ...................... 600/528, 586; 128/897; 206/305, 210, 363, 370, 459.1, 807

[56] References Cited

U.S. PATENT DOCUMENTS

| | | |
|---|---|---|
| 3,867,925 | 2/1975 | Ersek ........................................ 600/528 |
| 4,919,983 | 4/1990 | Fremin . |
| 5,269,314 | 12/1993 | Kendall et al. . |
| 5,294,375 | 3/1994 | Kampe et al. . |
| 5,322,031 | 6/1994 | Lerner et al. . |
| 5,365,023 | 11/1994 | Lawton . |
| 5,413,234 | 5/1995 | Hekal et al. . |
| 5,428,193 | 6/1995 | Mandiberg . |
| 5,528,004 | 6/1996 | Wurzburger . |

*Primary Examiner*—William E. Kamm
*Attorney, Agent, or Firm*—Michael I. Kroll

[57] ABSTRACT

A protective cover for a stethoscope with a chestpiece having a generally circular anterior surface which is placed against the skin of a patient during use, a generally circular outer rim, and a posterior surface. The cover is disposable and adapted to be removably secured to the chestpiece such that the cover completely covers the anterior surface and outer rim of the chestpiece, thereby physically isolating the anterior surface from contaminants, and further includes provision for effecting a visual change in the appearance of the cover when the stethoscope is used. The cover is preferably formed of a thin, elastomeric, liquid-impervious material and its appearance changes upon exposure to one or more of moisture, pressure, galvanic skin response and skin temperature.

12 Claims, 4 Drawing Sheets

SINGLE USE INDICATOR FOR STETHOSCOPES

BACKGROUND OF THE INVENTION

1. Field of the Invention

The instant invention relates generally to single use, disposable covers for protecting stethoscopes from contamination from contact with the patients skin. More specifically, it relates to stethoscope covers having a visually perceptible indication of use, so that the stethoscope user can readily determine if the stethoscope has been used, in order to ensure that contaminants are not transferred between patients. The invention also relates to single use disposable stethoscope chestpieces having a visually perceptible indication of use.

2. Description of the Prior Art

Protective stethoscope covers are known in the art. For example, U.S. Pat. No. 5,365,023 (Lawton, G.P., Nov.15, 1994) discloses an elastic, disposable cover for the head of stethoscope, formed of latex or a similar elastomeric material, preferably pre-shaped in a shallow parabola to facilitate installation and removal.

U.S. Pat. No. 5,428,193 (Mandiberg, R., Jun. 27, 1995) discloses a flexible, resilient and removable cover for temporarily covering the diaphragm portion of a stethoscope.

U.S. Pat. No. 5,528,004 (Wurzburger, I., Jun. 18, 1996) discloses a diskshaped structure having an adhesive backing for attachment to the diaphragm of the stethoscope.

BRIEF SUMMARY OF THE INVENTION

The present invention is concerned with the aseptic use of stethoscopes. Specifically, the invention relates to stethoscopes having a visually perceptible indication of use in combination with a disposable, single use structure which comes into physical contact with the patient.

A primary object of the present invention is to provide a protective stethoscope cover which reduces the chances of spreading contamination between patients by providing a visually perceptible indication that the cover has been used on a patient.

Another object of the present invention is to provide a protective stethoscope cover which can be removably attached to the chestpiece of a stethoscope and which undergoes a visually perceptible change upon contact with the skin of a patient.

An additional object of the present invention is to provide a protective stethoscope cover which undergoes a visually perceptible change in color or opacity as a result of exposure to one or more of moisture, pressure, skin temperature and galvanic skin response.

Another object of the present invention is to provide a protective stethoscope cover which is simple to make and easy to use.

Another object is to provide a protective stethoscope cover that is economical in cost to manufacture.

The foregoing and other objects, advantages and characterizing features will become apparent from the following description of certain illustrative embodiments o f the invention.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings. Attention is called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

DETAILED DESCRIPTION OF THE PREFERRED EMBODIMENTS

Figure 1:
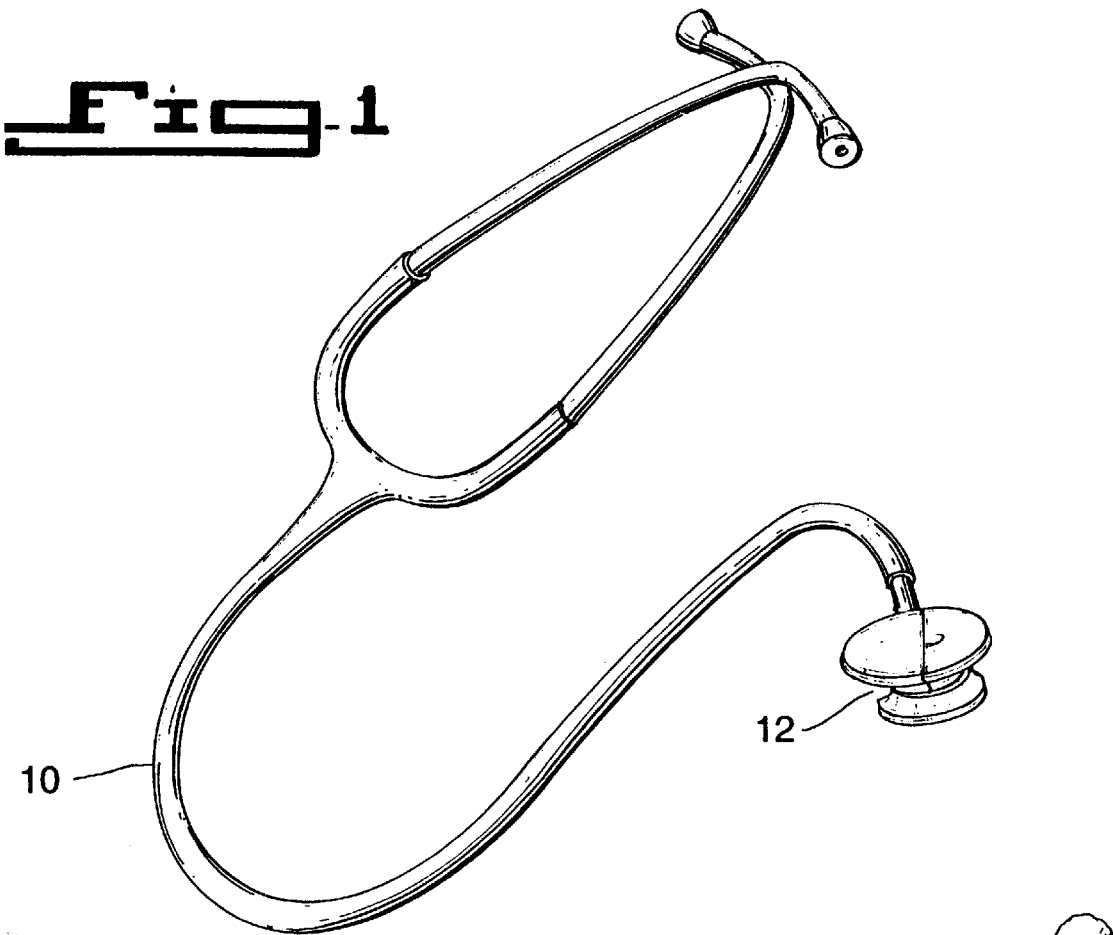
FIG. 1 is an overview of a stethoscope utilizing the single use stethoscope cover of the present invention.
Figure 2:
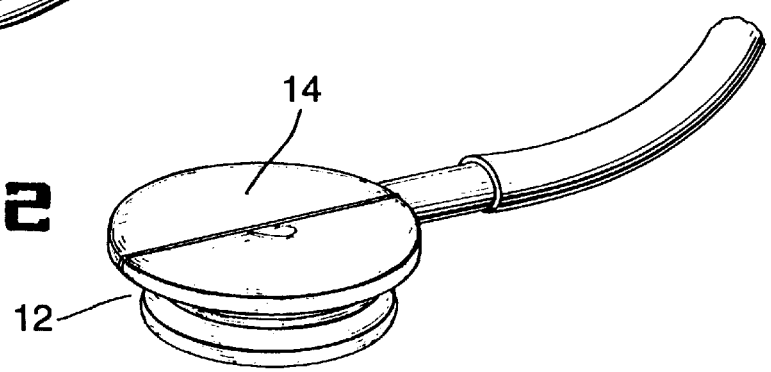
FIG. 2 is an enlarged view of a stethoscope chestpiece utilizing the single use stethoscope cover of the present invention.
Figure 3:
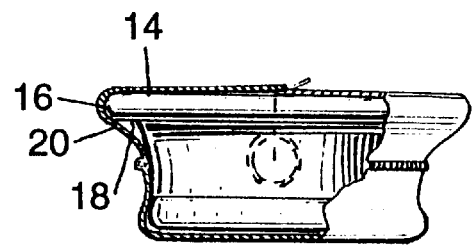
FIG. 3 is a cross-sectional view of a stethoscope chestpiece utilizing the single use stethoscope cover of the present invention.
Figure 4:
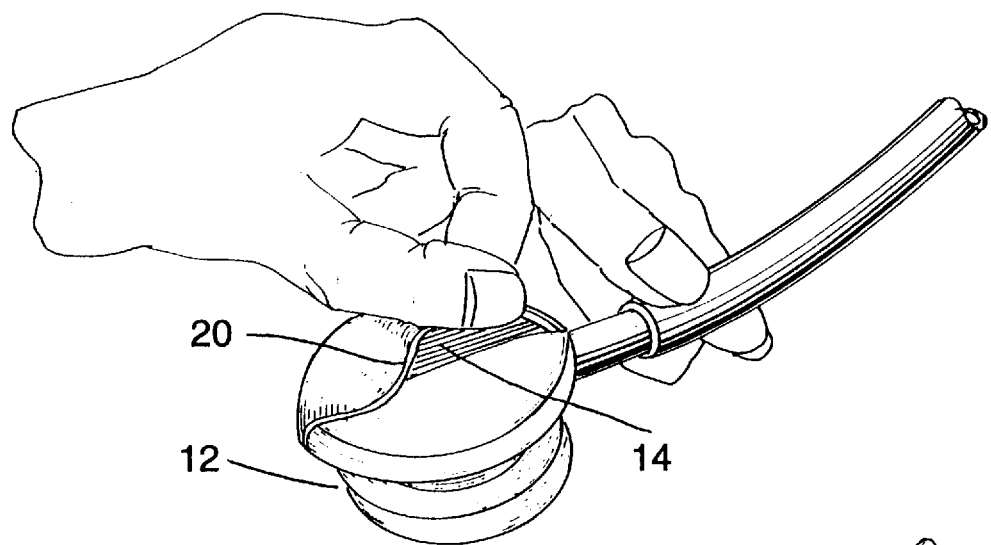
FIG. 4 is a view similar to that of FIG. 2, showing the manual removal of the single use stethoscope cover of the present invention.
Figure 5:
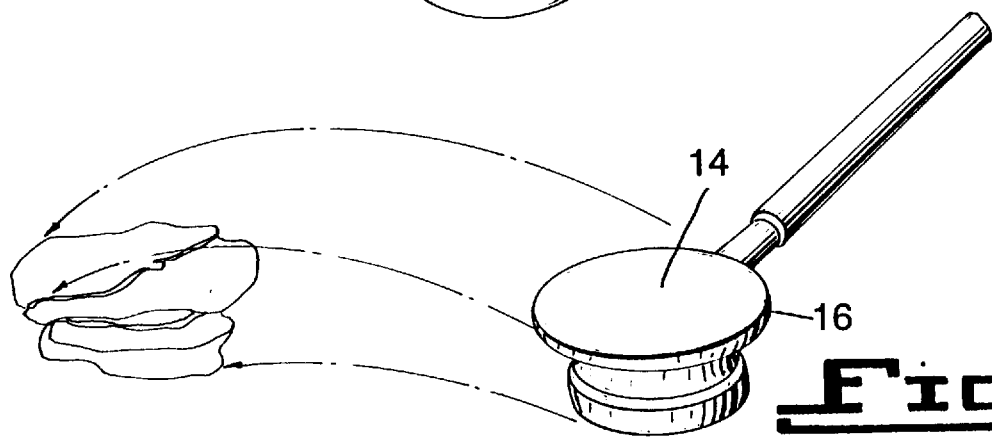
FIG. 5 is a view similar to that of FIG. 4, showing the stethoscope and single use stethoscope cover after removal.
Figure 6:
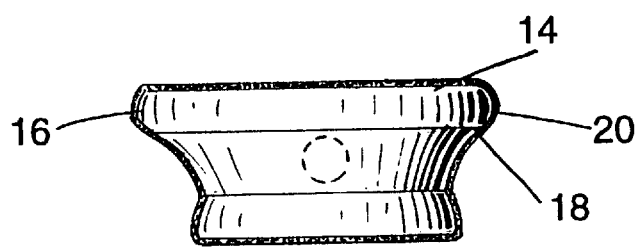
FIG. 6 is a side view of a stethoscope chestpiece utilizing the single use stethoscope cover of the present invention, with the stethoscope cover shown in cross-section.
Figure 7:
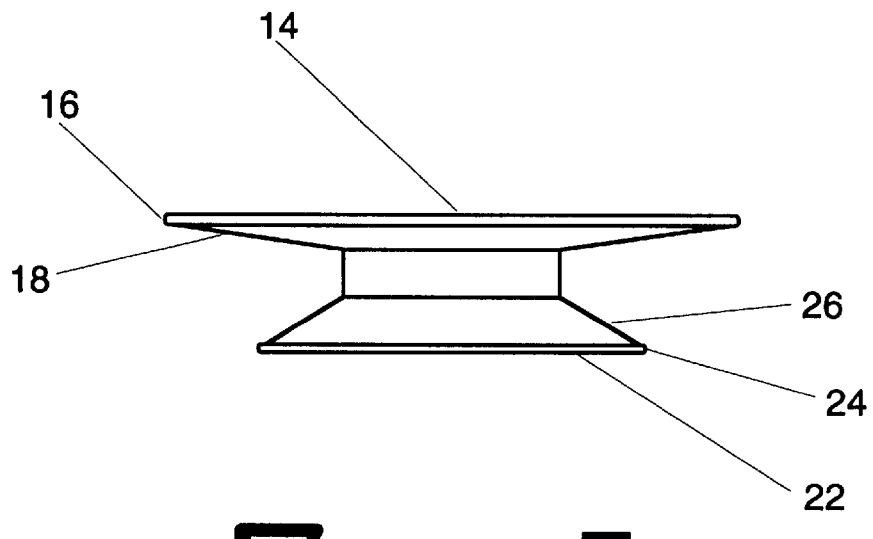
FIG. 7 is a side view of a stethoscope chestpiece.

Turning now descriptively to the drawings, in which similar reference characters denote similar elements throughout the several views, the Figures illustrate a single use stethoscope cover of the present invention. With regard to the reference numerals used, the following numbering is used throughout the various drawing figures.

10 stethoscope
12 chestpiece of stethoscope 10
14 generally circular anterior surface of chestpiece 12
16 generally circular outer rim of chestpiece 12
18 posterior surface of chestpiece 12
20 disposable cover for chestpiece 12
22 alternate anterior surface of chestpiece 12
24 alternate outer rim of chestpiece 12
26 alternate posterior surface of chestpiece 12
28 support layer of disposable cover 20
30 use indicating layer of disposable cover 20, before use 32 use indicating layer of disposable cover 20, after use 34 rolled peripheral edge of disposable cover 20

FIG. 1 through 10 illustrate a stethoscope cover 20 having a single use indicator adapted to be removably secured to the chestpiece 12 of a stethoscope 10. Speaking generally, most stethoscopes have a chestpiece 12 with a generally circular anterior surface 14 which is placed against the skin of a patient during use. The anterior surface is commonly referred to as a diaphragm. A generally circular outer rim 16 comprises the exterior circumference of the anterior surface 14 and the posterior surface 18. The stethoscope cover of the present invention is adapted to be removably secured to the chestpiece 12 such that the cover completely covers the anterior surface 14 and outer rim 16 of the chestpiece, thereby physically isolating the chestpiece from contamination. Many stethoscopes have dual, oppositely disposed surfaces, one being a diaphragm 14 for detecting high frequency sounds (about 200 Hz to about 500 Hz) and the other being a bell, shown in the Figures as alternate anterior surface 22, for detecting low frequency sounds (about 20 Hz to about 100 Hz). The present invention is intended to be used with either type of surface, diaphragm or bell. It is noted that, when the bell end is used, the only portion which generally comes into contact with the patient is the outer rim 24, with the alternate anterior surface more properly defined as a circular planar region coextensive with the outer rim. Nevertheless, the present invention functions equally well with either bell or diaphragm type pick-up.

In order to 1) protect the chestpiece from contamination and 2) allow normal functioning of the stethoscope, the cover is preferably made from a thin, elastomeric, liquid-impervious material such as, for example, latex. In its preferred embodiment, the cover is generally circular, or slightly parabolic, with an interior region which covers the anterior surface and outer rim, and an exterior, or peripheral edge region, which can be stretched over the outer rim so that it engages the posterior surface 18, 26 of the chestpiece, thereby providing complete coverage of the contact region of the chestpiece. It is preferred that the stethoscope cover of the present invention have a spiral rolled or raised edge 34, similar to that of a condom, in order to facilitate placement and removal, and also to ensure a snug fit. It can be readily appreciated that the edge portion should preferably have, at the least, 1) an unstretched diameter less than that of the outer rim, 2) elasticity sufficient to allow the edge portion to be stretched over the outer rim, and 3) resiliency sufficient to maintain engagement with the posterior surface during use.

The stethoscope cover of the present invention can take other forms than that described above, provided that the anterior surface of the chestpiece is completely covered. For example, a disk-shaped shield which attaches to the chestpiece with an adhesive backing, or a unitary, semi-rigid structure which snaps onto the chestpiece. The present invention is intended to encompass all forms of protective stethoscope covers, as long as they include a visually perceptible indication of use. This use indicator greatly improves the efficacy of the stethoscope cover by providing a readily detectable indication that the stethoscope cover has been used on a patient, is potentially contaminated, and should be replaced before the stethoscope is used on another patient. This avoids a major problem with known stethoscope covers, namely, that there is no way to determine if the cover has been used on a patient. It can be readily appreciated that reusing a protective stethoscope cover greatly diminishes its effectiveness in preventing the spread of contaminants between patients.

The visually perceptible indication of use can be triggered by one or more of various factors, all of which are within the scope of the invention. For example, the stethoscope covers of the present invention can be designed to change color or opacity when exposed to one or more of the following: moisture, pressure, skin temperature or galvanic skin response.

Figure 8:
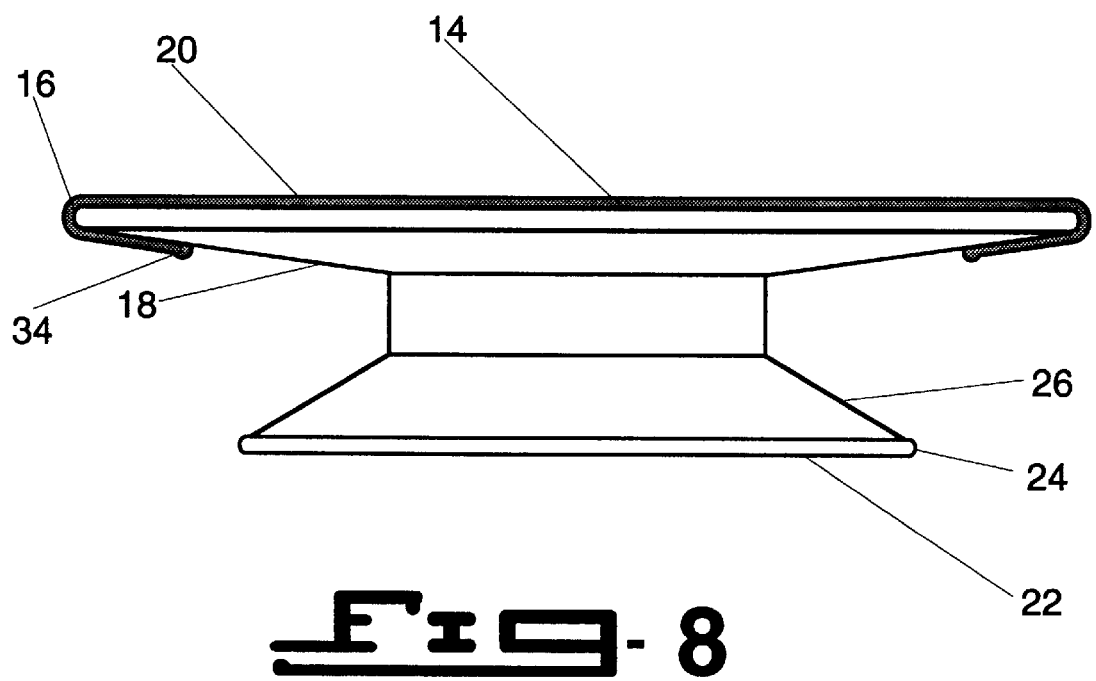
FIG. 8 is a side view of the stethoscope chestpiece of FIG. 7, utilizing a single use stethoscope cover of the present invention.
Figure 9:
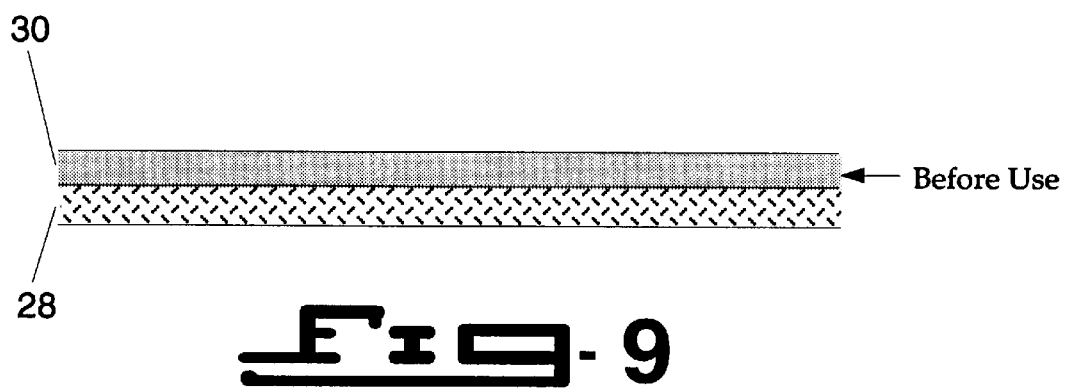
FIG. 9 is an enlarged, cross-sectional view of one embodiment of the single use stethoscope cover of the present invention, wherein the stethoscope cover material comprises a bilayer composite structure.
Figure 10:
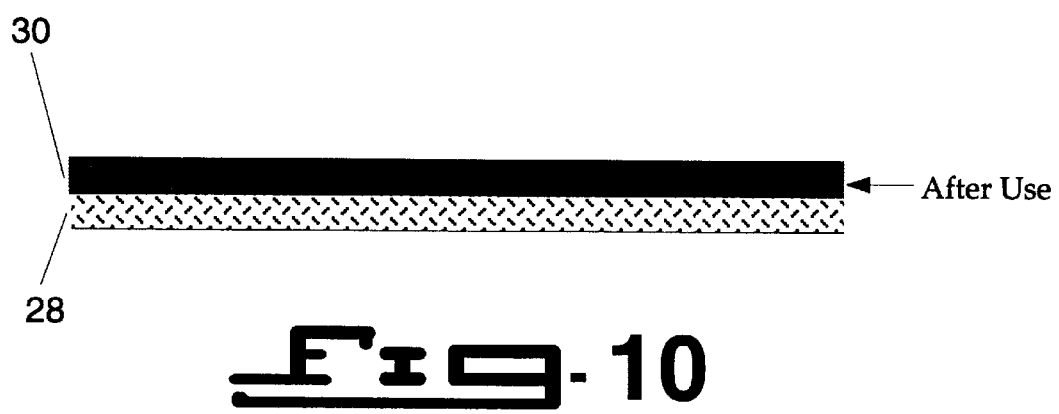
FIG. 10 is a view identical to that of FIG. 9, illustrating the visual change in appearance of one of the layers after use.

The visually perceptible use indicator can be either impregnated within the cover material, or can be disposed over the cover material as shown in FIGS. 8 and 9. If disposed over the cover material, the indicator can be either laminated securely over the cover or loosely oriented, such that the indicator is removed upon use, thus effecting the visual change.

Thermotropic materials are known in the art. See, for example, U.S. Pat. No. 4,188,437 (Rohowetz). Speaking generally, these materials include thermotropic dyes which exhibit a visible color change upon exposure to a specific threshold temperature. There are many thousands of compounds available which are thermochromic at various temperatures; selection is a simple design choice. For the instant invention, the thermotropic dye should exhibit a visible color change at a temperature of from about 90 to about 95° F. (about 32° to about 35° C.).

Materials which change color upon exposure to humidity are also known in the art. These materials include, for example, metallic salts which change color upon exposure to moisture or humidity, which exposure changes the salt from its dehydrated to its hydrated form. Examples include cobalt salts, such as cobaltous chloride, but again, there are many compounds to choose from, with the particular compound or combination of compounds a simple design choice.

Pressure sensitive compositions are also well known in the art, commonly comprising a plurality of adjacent dye layers which, when pressed together, combine sufficiently to exhibit a visible color change.

With regard to galvanic skin response, it is expected that conductive inks can be suitably employed in the present invention. For example, the cover can have on its surface a plurality of separate conductive ink patterns which are electrically connected to each other, whereby, upon being simultaneously placed in contact with skin, the patterns are actuated by resistor bridging, resulting in a perceptible change in the ink patterns.

It will be understood that each of the elements described above, or two or more together, may also find a useful application in other types of applications differing from the type described above. While the invention has been illustrated and described as embodied in a stethoscope cover with a single use indicator, it is not intended to be limited to the details shown, since it will be understood that various omissions, modifications, substitutions and changes in the forms and details of the formulation illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of this invention.

What is claimed as new and desired to be protected by letters patent is set forth in the appended claims:

I claim:

1. A single use indicator for a stethoscope with a chestpiece having a generally circular anterior surface which is placed against the skin of a patient during use, a generally circular outer rim, and a posterior surface, comprising:

a) a disposable cover formed of a thin, elastomeric, liquid-impervious material removably secured to the chestpiece such that said cover completely covers the anterior surface and outer rim of the chestpiece, thereby physically isolating the anterior surface from contaminants;

b) means for effecting a visual change in the appearance of said cover when the stethoscope is used; and c) said cover being elastic and generally circular or slightly parabolic with an interior portion and a peripheral edge portion, said peripheral edge portion having an unstretched diameter less than that of the outer rim of the chestpiece and stretched over the anterior surface and outer rim of the chestpiece in order to engage the posterior surface of the chestpiece so that said interior portion of said cover overlays the anterior surface of said chestpiece, and resilience which maintains said engagement with the posterior surface while said interior portion overlays the anterior surface of said chestpiece.

2. A single use indicator for a stethoscope with a chestpiece having a generally circular anterior surface which is placed against the skin of a patient during use, a generally circular outer rim, and a posterior surface, comprising:

a) a disposable cover removably secured to the chestpiece such that said cover completely covers the anterior surface and outer rim of the chestpiece, thereby physically isolating the anterior surface from contaminants; and b) means for effecting a visual change in the appearance of said cover when the stethoscope is used and said cover is exposed to moisture.

3. A single use indicator for a stethoscope with a chestpiece having a generally circular anterior surface which is placed against the skin of a patient during use, a generally circular outer rim, and a posterior surface, comprising:

a) a disposable cover removably secured to the chestpiece such that said cover completely covers the anterior surface and outer rim of the chestpiece, thereby physically isolating the anterior surface from contaminants; and b) means for effecting a visual change in the appearance of said cover when the stethoscope is used and said cover is exposed to pressure.

4. A single use indicator for a stethoscope with a chestpiece having a generally circular anterior surface which is placed against the skin of a patient during use, a generally circular outer rim, and a posterior surface, comprising:

a) a disposable cover removably secured to the chestpiece such that said cover completely covers the anterior surface and outer rim of the chestpiece, thereby physically isolating the anterior surface from contaminants; and b) means for effecting a visual change in the appearance of said cover when the stethoscope is used and said cover is exposed to galvanic skin response.

5. A single use indicator for a stethoscope with a chestpiece having a generally circular anterior surface which is placed against the skin of a patient during use, a generally circular outer rim, and a posterior surface, comprising:

a) a disposable cover removably secured to the chestpiece such that said cover completely covers the anterior surface and outer rim of the chestpiece, thereby physically isolating the anterior surface from contaminants; and b) means for effecting a visual change in the appearance of said cover when the stethoscope is used and said cover is exposed to skin temperature.

6. A single use indicator for a stethoscope with a chestpiece having a generally circular anterior surface which is placed against the skin of a patient during use, a generally circular outer rim, and a posterior surface, comprising:

a) a disposable cover removably secured to the chestpiece such that said cover completely covers the anterior surface and outer rim of the chestpiece, thereby physically isolating the anterior surface from contaminants; and b) means for effecting a visual change in the appearance of said cover when the stethoscope is used and said cover is exposed to pressure in combination with moisture.

7. A single use indicator for a stethoscope with a chestpiece having a generally circular anterior surface which is placed against the skin of a patient during use, a generally circular outer rim, and a posterior surface, comprising:

a) a disposable cover removably secured to the chestpiece such that said cover completely covers the anterior surface and outer rim of the chestpiece, thereby physically isolating the anterior surface from contaminants; and b) means for effecting a visual change in the appearance of said cover when the stethoscope is used and said cover is exposed pressure in combination with human skin temperature.

8. A single use indicator for a stethoscope with a chestpiece having a generally circular anterior surface which is placed against the skin of a patient during use, a generally circular outer rim, and a posterior surface, comprising:

a) a disposable cover formed of a thin, elastomeric, liquid-impervious material removably secured to the chestpiece such that said cover completely covers the anterior surface and outer rim of the chestpiece, thereby physically isolating the anterior surface from contaminants, said cover being comprised to two contiguous layers, a lower support layer and an upper use indicator layer; and b) means for effecting a visual change in the appearance of said cover when the stethoscope is used and said cover is exposed to moisture.

9. A single use indicator for a stethoscope as defined in claim 8, in which said upper use indicator layer includes a compound which exhibits a color change upon exposure to moisture.

10. A single use indicator for a stethoscope as defined in claim 9 in which said compound is a metallic salt.

11. A single use indicator for a stethoscope as defined in claim 8, in which said upper use indicator layer includes a compound which exhibits a color change upon exposure to pressure.

12. A single use indicator for a stethoscope as defined in claim 8, in which said upper use indicator layer includes a compound which exhibits a color change upon exposure to skin temperature.

* * * * *